(12) United States Patent
Conway et al.

(10) Patent No.: US 8,298,255 B2
(45) Date of Patent: Oct. 30, 2012

(54) CAP DISPLACEMENT MECHANISM FOR LANCING DEVICE AND MULTI-LANCET CARTRIDGE

(75) Inventors: William E. Conway, Smyrna, GA (US); Christopher J. Ruf, Marietta, GA (US); John C. Irwin, Woodstock, GA (US); Stephen J. Flynn, Peachtree City, GA (US); Avi M. Robbins, Longwood, FL (US); Brian D. VanHiel, Smyrna, GA (US); Brian D. Leutz, McDonough, GA (US); Richard W. LeVaughn, Newnan, GA (US); Michael V. Lipoma, Villa Rica, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 1399 days.

(21) Appl. No.: 11/931,023

(22) Filed: Oct. 31, 2007

(65) Prior Publication Data

US 2008/0065134 A1 Mar. 13, 2008

Related U.S. Application Data

(62) Division of application No. 11/107,984, filed on Apr. 15, 2005, now Pat. No. 7,377,904.

(60) Provisional application No. 60/562,712, filed on Apr. 16, 2004.

(51) Int. Cl.
*A61B 17/32* (2006.01)
*A61B 5/15* (2006.01)

(52) U.S. Cl. ...................................... 606/182

(58) Field of Classification Search .......... 606/181–183; 600/573–584; 604/207–211
See application file for complete search history.

(56) References Cited

U.S. PATENT DOCUMENTS

| | | |
|---|---|---|
| 3,760,809 A | 9/1973 | Campbell, Jr. |
| D228,815 S | 10/1973 | Campbell, Jr. |
| D245,040 S | 7/1977 | Thomas |
| 4,643,189 A | 2/1987 | Mintz |
| D297,978 S | 10/1988 | White |
| 4,794,926 A | 1/1989 | Munsch et al. |
| 4,823,806 A | 4/1989 | Bajada |
| 4,892,097 A | 1/1990 | Ranalletta et al. |
| 4,983,178 A | 1/1991 | Schnell |
| 4,995,402 A | 2/1991 | Smith et al. |
| 5,047,044 A | 9/1991 | Smith et al. |

(Continued)

FOREIGN PATENT DOCUMENTS

DE 4234553 A1 10/1992

(Continued)

*Primary Examiner* — Elizabeth Houston
(74) *Attorney, Agent, or Firm* — Gardner Groff Greenwald & Villanueva, PC

(57) ABSTRACT

A medical lancing device including a replaceable multi-lancet cartridge. The lancing device includes an advancing mechanism that advances lancets within the cartridge into an active position, separates a protective cap from the active lancet, and energize a drive mechanism of the lancing device. A cap displacement mechanism moves the separated cap out of the travel path of the active lancet. In a first example embodiment, the cap displacement mechanism includes a cantilevered spring arm that displaces the detached cap of the active lancet. In a second example embodiment, the cap displacement mechanism includes a spring-biased cam-driven plunger that displaces the detached cap of the active lancet. Then an activation mechanism releases the energized active lancet to traverse the unobstructed lancing stroke path to pierce the subject's skin at a desired lancing site.

16 Claims, 14 Drawing Sheets

U.S. PATENT DOCUMENTS

| | | | |
|---|---|---|---|
| 5,196,025 | A | 3/1993 | Ranalletta et al. |
| 5,318,583 | A | 6/1994 | Rabenau et al. |
| 5,318,584 | A | 6/1994 | Lange et al. |
| 5,395,388 | A | 3/1995 | Schraga |
| 5,464,418 | A | 11/1995 | Schraga |
| 5,477,209 | A | 12/1995 | Benson, Jr. et al. |
| 5,507,288 | A | 4/1996 | Bocker et al. |
| 5,514,152 | A | 5/1996 | Smith |
| 5,527,334 | A | 6/1996 | Kanner et al. |
| 5,535,743 | A | 7/1996 | Backhaus et al. |
| 5,551,422 | A | 9/1996 | Simonsen et al. |
| D376,203 | S | 12/1996 | Schraga |
| 5,628,764 | A | 5/1997 | Schraga |
| 5,645,555 | A | 7/1997 | Davis et al. |
| 5,676,143 | A | 10/1997 | Simonsen et al. |
| 5,692,504 | A | 12/1997 | Essenpreis et al. |
| 5,710,630 | A | 1/1998 | Essenpreis et al. |
| 5,713,352 | A | 2/1998 | Essenpreis et al. |
| 5,734,587 | A | 3/1998 | Backhaus et al. |
| RE35,803 | E | 5/1998 | Lange et al. |
| 5,770,454 | A | 6/1998 | Essenpreis et al. |
| 5,776,157 | A | 7/1998 | Thorne et al. |
| 5,786,226 | A | 7/1998 | Bocker et al. |
| 5,825,488 | A | 10/1998 | Kohl et al. |
| 5,879,373 | A | 3/1999 | Roper et al. |
| 5,962,852 | A | 10/1999 | Knuettel et al. |
| 5,971,941 | A | 10/1999 | Simons et al. |
| 5,986,770 | A | 11/1999 | Hein et al. |
| 5,997,561 | A | 12/1999 | Bocker et al. |
| 6,010,519 | A | 1/2000 | Mawhirt et al. |
| 6,036,924 | A | 3/2000 | Simons et al. |
| 6,042,595 | A | 3/2000 | Morita |
| 6,071,294 | A | 6/2000 | Simons et al. |
| 6,093,156 | A | 7/2000 | Cunningham et al. |
| 6,144,449 | A | 11/2000 | Knuettel et al. |
| 6,156,050 | A | 12/2000 | Davis et al. |
| 6,168,606 | B1 | 1/2001 | Levin et al. |
| 6,210,421 | B1 | 4/2001 | Bocker et al. |
| 6,228,100 | B1 * | 5/2001 | Schraga ............ 606/183 |
| D444,557 | S | 7/2001 | Levaughn et al. |
| D447,566 | S | 9/2001 | Levaughn et al. |
| 6,306,152 | B1 | 10/2001 | Verdonk et al. |
| 6,330,063 | B1 | 12/2001 | Knuettel et al. |
| D458,127 | S | 6/2002 | De Groote |
| 6,418,339 | B1 | 7/2002 | Essenpreis et al. |
| 6,432,120 | B1 | 8/2002 | Teo |
| 6,472,220 | B1 | 10/2002 | Simons et al. |
| 6,531,702 | B1 | 3/2003 | Mischler et al. |
| 6,540,675 | B2 | 4/2003 | Aceti et al. |
| 6,584,335 | B1 | 6/2003 | Haar et al. |
| 6,616,616 | B2 | 9/2003 | Fritz et al. |
| 6,706,159 | B2 | 3/2004 | Moerman et al. |
| 6,783,537 | B1 | 8/2004 | Kuhr et al. |
| 6,852,119 | B1 | 2/2005 | Abulhaj et al. |
| 6,929,649 | B2 | 8/2005 | Pugh |
| 6,966,880 | B2 | 11/2005 | Boecker et al. |
| 6,988,996 | B2 | 1/2006 | Roe et al. |
| 7,001,344 | B2 | 2/2006 | Freeman et al. |
| 7,025,774 | B2 | 4/2006 | Freeman et al. |
| 7,041,068 | B2 | 5/2006 | Freeman et al. |
| 7,141,058 | B2 | 11/2006 | Briggs et al. |
| 2002/0052618 | A1 | 5/2002 | Haar et al. |
| 2002/0120216 | A1 | 8/2002 | Fritz et al. |
| 2002/0130042 | A1 | 9/2002 | Moerman et al. |
| 2002/0168290 | A1 | 11/2002 | Yuzhakov et al. |
| 2003/0013992 | A1 | 1/2003 | Uchigaki et al. |
| 2003/0073089 | A1 | 4/2003 | Mauze et al. |
| 2003/0073931 | A1 | 4/2003 | Boecker et al. |
| 2003/0083685 | A1 | 5/2003 | Freeman et al. |
| 2003/0083686 | A1 | 5/2003 | Freeman et al. |
| 2003/0088191 | A1 | 5/2003 | Freeman et al. |
| 2003/0143113 | A2 | 7/2003 | Yuzhakov et al. |
| 2003/0144608 | A1 | 7/2003 | Kojima et al. |
| 2003/0144609 | A1 | 7/2003 | Kennedy |
| 2003/0153939 | A1 | 8/2003 | Fritz et al. |
| 2003/0185713 | A1 | 10/2003 | Leonard et al. |
| 2003/0199789 | A1 | 10/2003 | Boecker et al. |
| 2003/0199790 | A1 | 10/2003 | Boecker et al. |
| 2003/0199791 | A1 | 10/2003 | Boecker et al. |
| 2003/0199893 | A1 | 10/2003 | Boecker et al. |
| 2003/0199894 | A1 | 10/2003 | Boecker et al. |
| 2003/0199895 | A1 | 10/2003 | Boecker et al. |
| 2003/0199896 | A1 | 10/2003 | Boecker et al. |
| 2003/0199897 | A1 | 10/2003 | Boecker et al. |
| 2003/0199898 | A1 | 10/2003 | Boecker et al. |
| 2003/0199899 | A1 | 10/2003 | Boecker et al. |
| 2003/0199900 | A1 | 10/2003 | Boecker et al. |
| 2003/0199901 | A1 | 10/2003 | Boecker et al. |
| 2003/0199902 | A1 | 10/2003 | Boecker et al. |
| 2003/0199903 | A1 | 10/2003 | Boecker et al. |
| 2003/0199904 | A1 | 10/2003 | Boecker et al. |
| 2003/0199905 | A1 | 10/2003 | Boecker et al. |
| 2003/0199906 | A1 | 10/2003 | Boecker et al. |
| 2003/0199907 | A1 | 10/2003 | Boecker et al. |
| 2003/0199908 | A1 | 10/2003 | Boecker et al. |
| 2003/0199909 | A1 | 10/2003 | Boecker et al. |
| 2003/0199910 | A1 | 10/2003 | Boecker et al. |
| 2003/0199911 | A1 | 10/2003 | Boecker et al. |
| 2003/0211619 | A1 | 11/2003 | Olson et al. |
| 2003/0212344 | A1 | 11/2003 | Yuzhakov et al. |
| 2003/0212345 | A1 | 11/2003 | McAllister et al. |
| 2003/0212347 | A1 | 11/2003 | Sohrab |
| 2003/0212424 | A1 | 11/2003 | Briggs et al. |
| 2003/0223906 | A1 | 12/2003 | McAllister et al. |
| 2004/0009100 | A1 | 1/2004 | Simons et al. |
| 2004/0010279 | A1 | 1/2004 | Freeman et al. |
| 2004/0039303 | A1 | 2/2004 | Wurster et al. |
| 2004/0049219 | A1 | 3/2004 | Briggs et al. |
| 2004/0049220 | A1 | 3/2004 | Boecker et al. |
| 2004/0064068 | A1 | 4/2004 | DeNuzzio et al. |

FOREIGN PATENT DOCUMENTS

| | | |
|---|---|---|
| FR | 2797579 | 2/2001 |
| JP | 2000245715 A | 9/2000 |

* cited by examiner

CAP DISPLACEMENT MECHANISM FOR LANCING DEVICE AND MULTI-LANCET CARTRIDGE

CROSS REFERENCE TO RELATED APPLICATIONS

This application is a divisional of U.S. Non-Provisional patent application Ser. No. 11/107,984, filed Apr. 15, 2005, which claims the priority benefit of U.S. Provisional Patent Application Ser. No. 60/562,712, filed Apr. 16, 2004, the entireties of which are hereby incorporated herein by reference for all purposes.

TECHNICAL FIELD

The present invention relates generally to medical devices and procedures and, more particularly to cartridge assemblies for lancing devices for the collection and/or analysis of samples of blood or other bodily fluids.

BACKGROUND OF THE INVENTION

Many medical procedures require puncturing of the skin, and sometimes underlying tissues, of an animal or human subject. For example, a sharp lancet tip is commonly used to puncture the subject's skin at a lancing site to obtain a sample of blood, interstitial fluid, or other body fluid, as for example in blood glucose monitoring by diabetics and in blood typing and screening applications.

In some instances, a person must periodically sample their blood for multiple testing throughout the day or week. Because re-use of a lancet can result in infection or spread of blood-borne contaminants, persons requiring repeated testing often must carry around multiple lancets that are separately loaded into a lancing device for each sampling. This can be inconvenient and may lead to reduced compliance with a prescribed test regimen.

Accordingly, it has been discovered that needs exist for an improved lancing device capable of carrying out multiple sampling procedures without the need for separately loading individual lancets. It has also been discovered that needs exist for a convenient, disposable multi-lancet cartridge that can be loaded into a multi-use lancing device for carrying out multiple sampling procedures, and then be removed and replaced when fully or partially spent or when replacement is otherwise desired. It is to the provision of an improved sampling device and cartridge meeting these and other needs that the present invention is primarily directed.

SUMMARY OF THE INVENTION

Briefly described, in one aspect, the present invention is a lancing device comprising an outer housing for receiving a replaceable cartridge. Preferably, the cartridge includes a static outer shell that remains stationary relative to the housing and drive mechanism of the lancing device, and an array of lancets that are rotationally advanced within the outer shell and sequentially indexed through an active position for carrying out multiple lancing procedures. The cartridge preferably includes a rotationally moveable carrier for retaining and rotationally advancing the radial array of lancets within the outer shell, and for constraining the active lancet along a controlled and pre-defined path of travel during the lancing stroke. The cartridge preferably also includes recesses, clips or other retainers for retaining protective endcaps that have been removed from the lancets out of the path of travel of the lancets, and preventing the caps from rattling around within the housing.

The lancing device preferably includes a drive mechanism, including for example a pair of opposed biasing mechanisms (e.g., springs) working in tandem, to drive and return the plunger mechanism of the lancing device and propel the active lancet through its lancing stroke. In example embodiments, the jaw of the drive mechanism engages the active lancet from the bottom only, through a slot in the cartridge shell, so that a partially spent cartridge can be removed from the lancing device and reinserted for use at a later time. In further example embodiments, the lancing device includes a one-way clutch or ratchet mechanism to advance lancets sequentially through the active position and to prevent re-use of lancets. The lancing device preferably also includes an advancing and charging mechanism for sequentially indexing the lancet carrier, charging the drive mechanism, and detaching the endcap of the lancet at a controlled retraction rate during de-capping, all with a single and continuous operation.

The lancing device optionally includes a depth ring for adjusting the depth of penetration of the lancet. Preferably, the depth ring has a plurality of openings with varying opening sizes and varying countersink depths, and is rotatable through a sequence of positions adjacent the lancet opening in the housing of the lancing device, thereby forming a rotating shutter window, providing a wide range of depth control. In further example embodiments, the lancing device includes an improved activating button operable to activate the drive mechanism, and including an integral spring arm for biasing the activating button outwardly and a retainer for securing the rotating depth ring.

In another aspect, the invention is an improved cartridge assembly for use with a multi-use lancing device. The cartridge assembly preferably includes a plurality of penetration elements or lancets, each having its own protective covering or endcap, arranged for sequential use in piercing the skin or other tissue of a human or animal subject for obtaining a sample of blood, interstitial fluid, and/or other body fluid(s). In example embodiments, the cartridge has an outer shell or housing and a carrier assembly rotationally enclosed within the outer shell for retaining the lancets. Because the carrier rotationally advances the lancets within the outer shell of the cartridge, only one opening through the shell is required for allowing passage of the active lancet tip upon actuation of the device, thereby reducing the potential for contamination or accidental needle sticks.

And in yet another aspect, the present invention is a cap displacement mechanism that moves a sterility cap, after it has been separated from the active lancet, out of the lancing stroke travel path of the active lancet. In a first example embodiment, the cartridge includes a cantilevered spring arm that is mounted within the cartridge shell to bias the separated lancet cap out of the path of the lancing stroke. In a second example embodiment, the lancing device includes a spring-biased plunger that is driven along a cam surface of the lancing device to engage a lancet cap and push it transversely out of the path of the lancing stroke. In both embodiments, the carrier defines transverse guide paths near its outer perimeter for directing and retaining the lancet caps out of the travel path of the lancet tip. The transverse guide paths are preferably defined by one or more guide tracks (e.g., resilient fingers, barbs, or other engagement features) extending from the carrier for positively retaining the lancet caps that have been removed from the lancet bodies.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 15b is a detailed plan view of the advancer mechanism of FIG. 6, including the portion shown in FIG. 15a.

DETAILED DESCRIPTION OF EXAMPLE EMBODIMENTS

Figure 1:
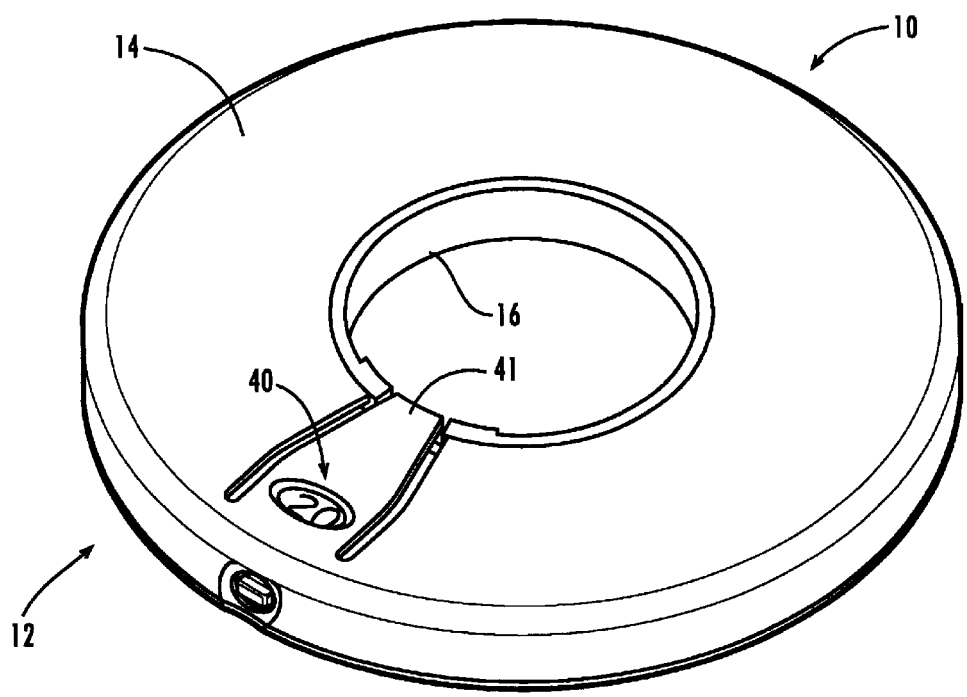
FIG. 1 is a perspective view of a multi-lancet cartridge assembly for a lancing device in accordance with a first example embodiment of the present invention.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

In its various embodiments, the present invention provides a lancet cap displacement mechanism that moves a cap, after it has been separated from an active lancet, out of the lancing stroke travel path of the active lancet. In a first example embodiment, the cap displacement mechanism is embodied in a replaceable multi-lancet cartridge for use in combination with a multi-use lancing device. In a second example embodiment, the cap displacement mechanism is embodied in a multi-use lancing device for use in combination with an improved replaceable multi-lancet cartridge.

The improvements of the present invention are adaptable for application in connection with various forms of multi-lancet lancing devices. In particular, the improvements of the present invention are of potential application to the multi-lancet lancing devices and replaceable multi-lancet cartridges shown in PCT International Publication No. WO 03/071940 A1 (International Application No. PCT/US03/05159, filed Feb. 20, 2003), which is hereby incorporated herein by reference. It will be recognized that the improvements disclosed herein are of individual advantage, or can be used in combination with one another.

In general, the lancing device of the present invention comprises a housing defining a chamber for receiving the cartridge; a drive mechanism for propelling an active lancet of the cartridge through a lancing stroke, from a retracted position within the cartridge to an advanced position wherein a sharp tip of the active lancet projects through a lancet opening in the housing to pierce the subject's skin at an intended lancing site; a charging mechanism for energizing the drive mechanism; and an advancing mechanism for sequentially advancing lancets of the cartridge into and through the active position. Various of these mechanisms can be combined; for example, a single mechanism optionally serves to energize the drive mechanism and simultaneously or sequentially advance the cartridge.

It will be understood that the lancet cap displacement mechanisms of the present invention may be embodied in a variety of styles of lancet cartridges and lancing devices. For example, the cap displacement mechanisms can be adapted for use in a cartridge having a radial arrays of lancets (as described herein), a linear array of lancets, a cylindrical array of axially arranged lancets, or other lancet and carrier configurations. And the cap displacement mechanisms can be adapted for use in disposable multi-lancet lancing devices (without a replaceable cartridge), with the components of the cap displacement mechanisms being elements of the lancing devices.

1. The Cartridge Assembly

Figure 2:
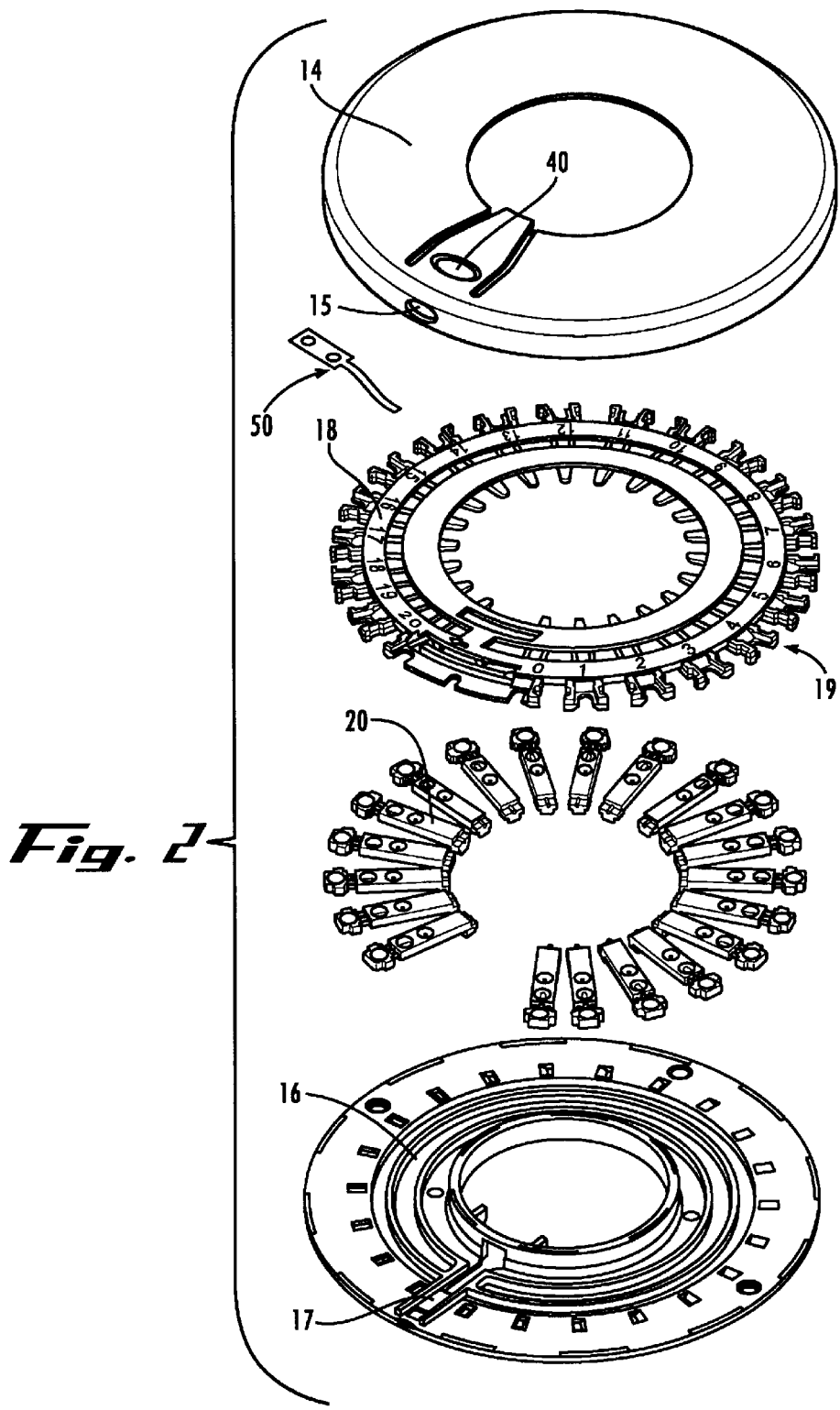
FIG. 2 is an exploded perspective view of the cartridge assembly of FIG. 1, showing a base housing, lancet array, carrier disk, spring-arm cap displacer, and cover housing.

With reference now to the drawing figures, FIGS. 1 and 2, as a perspective and exploded view respectively, show a cartridge assembly according to a first example embodiment of the present invention, which as a whole is designated by the reference number 10. The cartridge assembly 10 comprises a housing 12 for an array of lancets 20. The housing 12 preferably has two portions that connect together, for example, a top portion or cover 14 and a bottom portion or base 16. The top portion 14 and the bottom portion 16 preferably comprise generally circular disk-like structures with generally circular central aligned openings. The bottom portion 16 preferably has guides thereon or therein for engaging and guiding a rotatable carrier disk 18. When secured to together, the top portion 14 and the bottom portion 16 collectively form an annular outer shell of the cartridge assembly 10 for containing the carrier 18 and the array of lancets 20. In addition, the top cover 14 preferably defines a single lancet opening 15 on its outer circumferential rim, through which the tip of an active one of the lancets 20 passes during its lancing stroke.

The carrier disk 18 preferably includes guide channels 19 for permitting radial sliding movement of the lancets 20 in a lancing stroke between a retracted position and an extended position during the lancing operation. The guide channels 19 may be formed by projections on or recesses in the face of the carrier disk 18. In an example embodiment, the carrier 18 comprises twenty radial guide channels 19 for holding twenty lancets 20. The carrier 18 may, however, be provided with more or less guide channels 19 and lancets 20, as desired.

The lancets 20 are radially arranged in the rotatable carrier disk 18 in the guide channels 19, and can be driven through their lancing strokes in their axial direction (i.e., along a radius of the carrier disk 18) upon actuation of the lancing device. The cartridge assembly 10 is arranged such that the carrier disk 18, loaded with the lancets 20, is rotatably mounted on the bottom portion 16 of the housing 12. The top portion 14 of the housing 12 is then secured to the bottom portion 16, for example by ultrasonic welding, such that the carrier disk 18 and the lancets 20 can rotate within the housing 12. A one-way clutch or ratchet mechanism preferably limits the rotation of the carrier disk to rotation in a single direction to prevent re-use of a lancet and resultant potential contamination.

Figure 3:
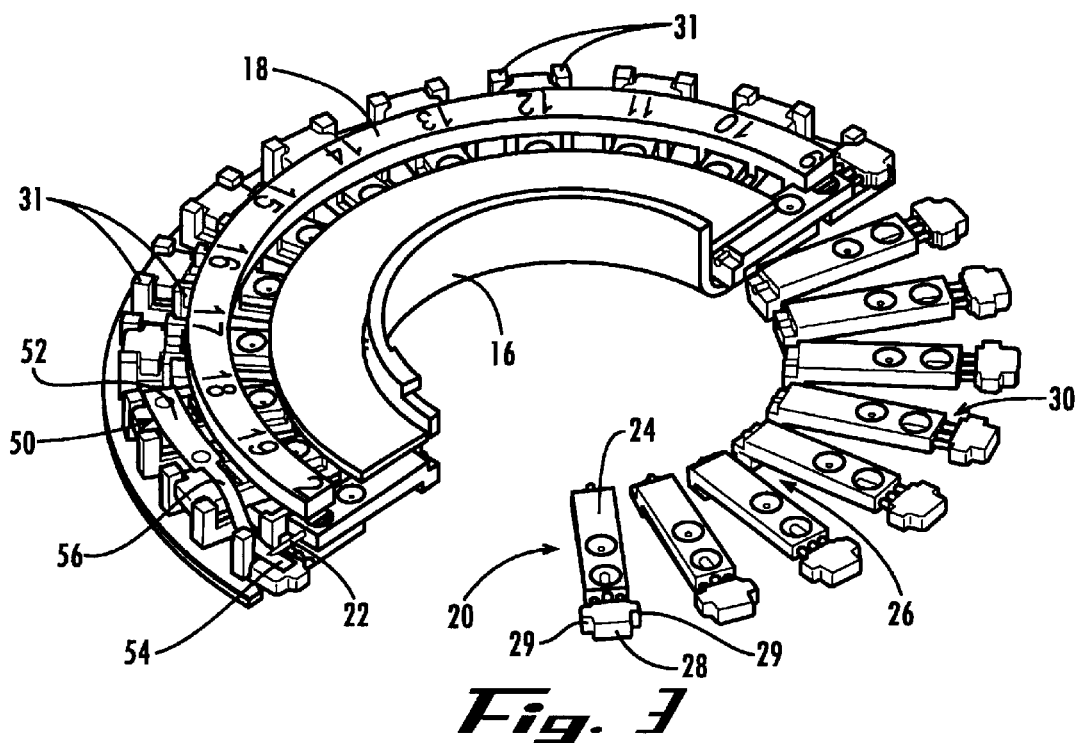
FIG. 3 is a cutaway perspective view of the lancet array, carrier, and spring arm of FIG. 2, showing spring arm displacing a separated cap of an active lancet.
Figure 4:
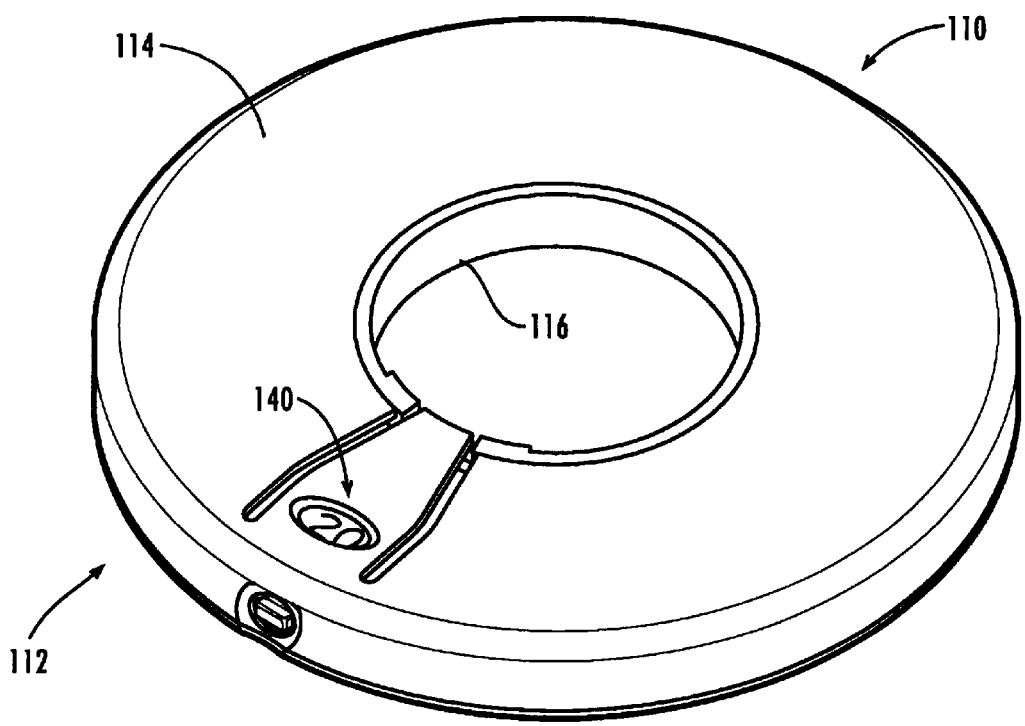
FIG. 4 is a perspective view of a cartridge assembly for a lancing device in accordance with a second example embodiment of the present invention.
Figure 5:
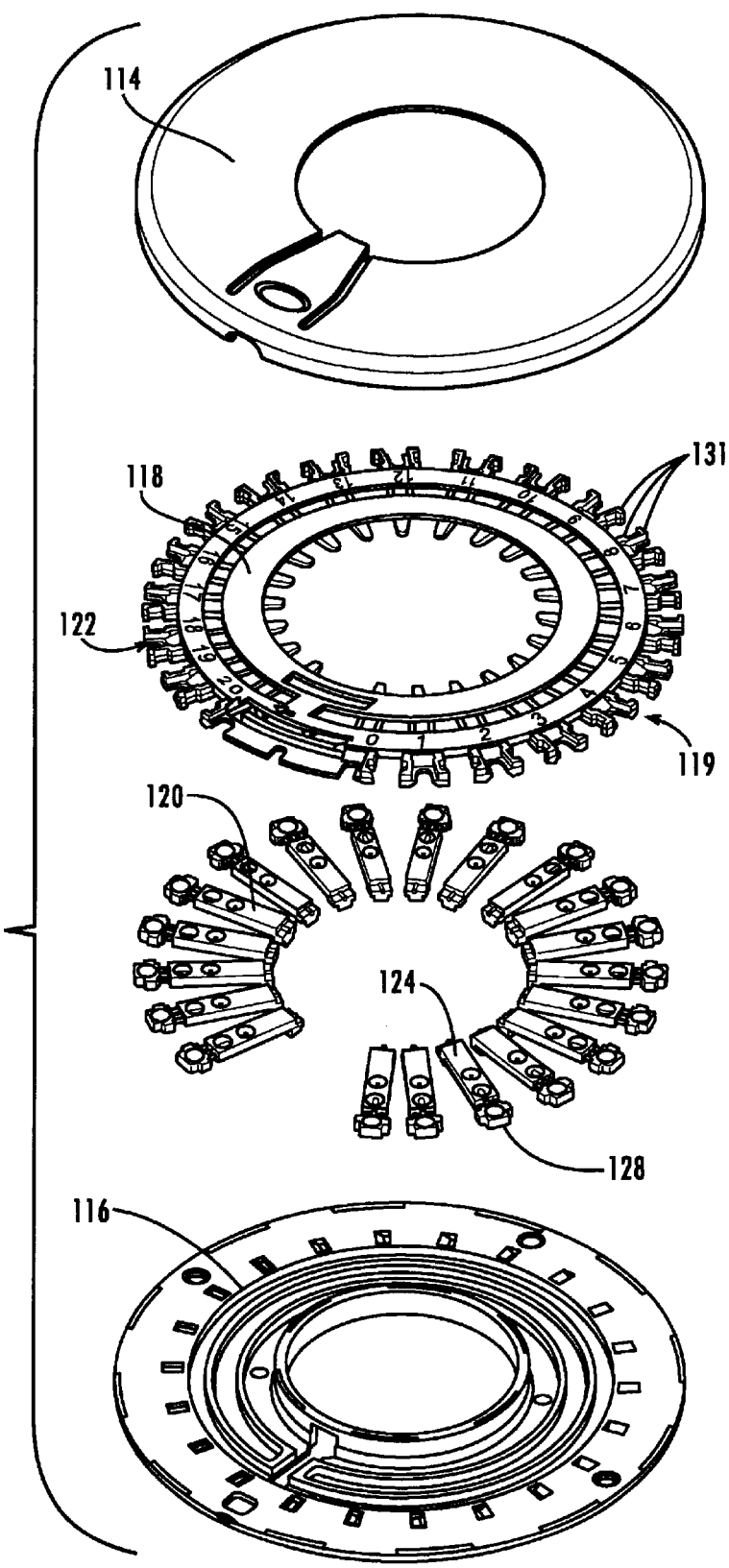
FIG. 5 is an exploded perspective view of the cartridge assembly of FIG. 4, showing a base housing, lancet array, carrier disk, and cover housing.

Referring additionally to FIG. 3, the lancets 20 each preferably comprise a needle or blade forming a sharp lancet tip 22, and a lancet body 24, and are preferably arranged generally radially in the guide channels 19 of the carrier disk 18 with their tips 22 directed outwardly. Preferably, the lancet body 24 is formed of plastic and is injection-molded around the lancet tip 22. Each lancet tip 22 is preferably encapsulated by a protective endcap 28, which may be integrally molded with the lancet body 24 and forms a sterility and safety barrier for the lancet tip.

The protective cap 28 of each lancet 20 is preferably connected to the body 24 by one or more thin segments or a reduced-thickness transition region such as a notch or slit, which forms a weaker separation zone that gives easily so that the cap can be removed. When the lancing device is charged or cocked (i.e., when the plunger of the drive mechanism pulls the lancet body 24 radially inwardly to energize the drive mechanism), the separation zone 30 fails and allows the protective cap 28 to easily detach from the lancet body 24. Alternatively, for lancets having caps that are discrete structures, the separation zone is defined by the gap between the cap and the lancet body.

Each lancet body 24 has a retainer that engages a cooperating structure of the lancing device's drive mechanism (described below) when the lancet is in the active position. For example, each lancet body 24 may have a retainer foot 26 extending downward from the back of the lancet body 24 to engage a cooperating jaw or other structure of the drive mechanism's reciprocating plunger when the lancet is in the active position. The feet 26 of the lancets 20 that are not in the active position preferably slide within a curved foot channel in the cartridge bottom housing 16 to constrain the used lancets against movement in the radial direction unless the lancet is in the active position.

The cartridge bottom housing 16 preferably defines a radial lancing channel 17 extending from the curved foot channel at a position corresponding to the lancet opening 15 in the cartridge top housing 14. The active lancet slides in the lancing channel 17 as it is driven along the lancing stroke upon activation or firing of the lancing device.

One or more cap surfaces 29 are engaged and constrained by cooperating cap guide tracks 31 of the carrier 18. The cap surfaces 29 may be defined by two shoulders projecting laterally outwardly on opposite sides of the cap 28, as shown, or by other features such as recesses formed into the caps. The cap guide tracks 31 hold unused lancets 20 in position on the carrier 18 prior to use, and to hold the cap 28 as the active lancet body 24 is retracted upon charging or energizing of the drive mechanism to detach the cap. The cap guide tracks 31 preferably define a transverse guide path (i.e., out of the plane of the lancet array, preferably at about 90 degrees relative to the lancing stroke travel path) along which the cap 28 is moved after it is detached from the lancet body 24. This transverse guide path allows removal of the cap 28 from the path of travel of the active lancet 20 as it is driven through its lancing stroke upon activation. The cap guide tracks 31 preferably comprise one or more resilient fingers or barbs for guiding the detached cap 28 along the transverse guide path and retaining the cap in its transversely displaced position so that it is prevented from rattling around within the housing 12 or potentially interfering with the device's operation. As an example, four cap guide track fingers 31 may be provided for receiving and guiding the two cap shoulder surfaces 29, as shown. Alternatively, two cap guide track fingers may be provided for guiding and being received by two cap recessed surfaces.

As shown in FIGS. 1 and 3, the carrier disk 18 can optionally be labeled with numbers or other indicia to indicate the number of unused lancets 20 remaining (or alternatively the number of lancets already used). The cartridge housing 12 preferably has an opening 40 therethrough, and the lancing device has a corresponding opening, such that the user can view the indicia.

The cartridge 10 preferably has a resilient member that is biased into engagement with an underlying lancet 20 in the active position. The resilient member thus prevents said active lancet 20 from being displaced if the cartridge 10 is removed from the lancing device after the device is charged and the cap is detached, at which point the active lancet would otherwise be unconstrained. The resilient member preferably comprises a resilient tongue portion 41 formed by a pair of cutout slots defined in the top housing cover 14 of the cartridge 10. When the cartridge 10 is installed in the lancing device, a cooperating portion of the drive mechanism flexes the tongue 41 out of contact with the active lancet, freeing it to traverse its lancing stroke upon actuation of the lancing device. In an alternate embodiment, the carrier is partially indexed within the cartridge housing (for example, a half-step forward or back, to a position between adjacent lancets), when the cartridge is removed from the lancing device, to prevent displacement of an unconstrained lancet from the active position.

a. Spring-Actuated Displacement of End-Caps

In this first example embodiment, the lancet cap displacement mechanism is provided by a cantilevered spring member 50 that serves to press the detached protective cap 28 of each sequential active lancet 20 along the transverse guide path and out of the radial path of travel of that lancet prior to activation or firing. The spring member 50 preferably has a first section 52, a second section 54, and an intermediate section 56. The first section 52 is attached (by conventional fastening structures or techniques) to the inner surface of the top portion 14 of the housing 12, or to another stationary part of the cartridge 10. The second section 54 is configured to engage the protective cap 28 and to push the cap 28 downwardly along the cap guide tracks 31 of the carrier 18, towards the bottom portion 16 of the housing 12. The intermediate section 56 connects the first section 52 to the second section 54.

In a typical commercial embodiment, the spring member 50 is leaf spring-type spring member, comprising a flexible, resilient piece of metal or other material that does not readily take on a set permanent deformation. The first section 52, the second section 54, and the intermediate section 56 each include an elongated member. And the intermediate section 56 is angled or curved downwardly from the first section 52 to the second section 54, thereby offsetting the first and second sections. In this way, the spring member 50 rides along the top surface of a lancet's endcap 28 as that lancet is advanced into the active position, and the spring member 50 flexes upwardly and is charged to impart a downward force on the cap. Then upon detachment of the cap 28 from the active lancet 20 by the retraction of the lancet body 24, the cap is pressed down along the guide tracks 31 under the influence of the charged spring member 50.

In an alternative embodiment, the leaf spring-type spring member 50 is inverted and attached to the housing bottom 16. In another alternative embodiment, the member 50 is a coil spring, with one end (the first section 52) attached to the housing 12 and the other end (the second section 54) including a ramped extension panel for riding along the caps as they are rotated to the active position.

b. Cam-Actuated Displacement of End-Caps

Referring now to FIGS. 4-9, a second example embodiment of the present invention will be described. The cartridge assembly 100 is substantially similar to the cartridge assembly 10 described above, having a housing 112 with top and bottom sections 114 and 116, a carrier 118, and an array of lancets 120 each having a body 124 and a cap 28.

Figure 6:
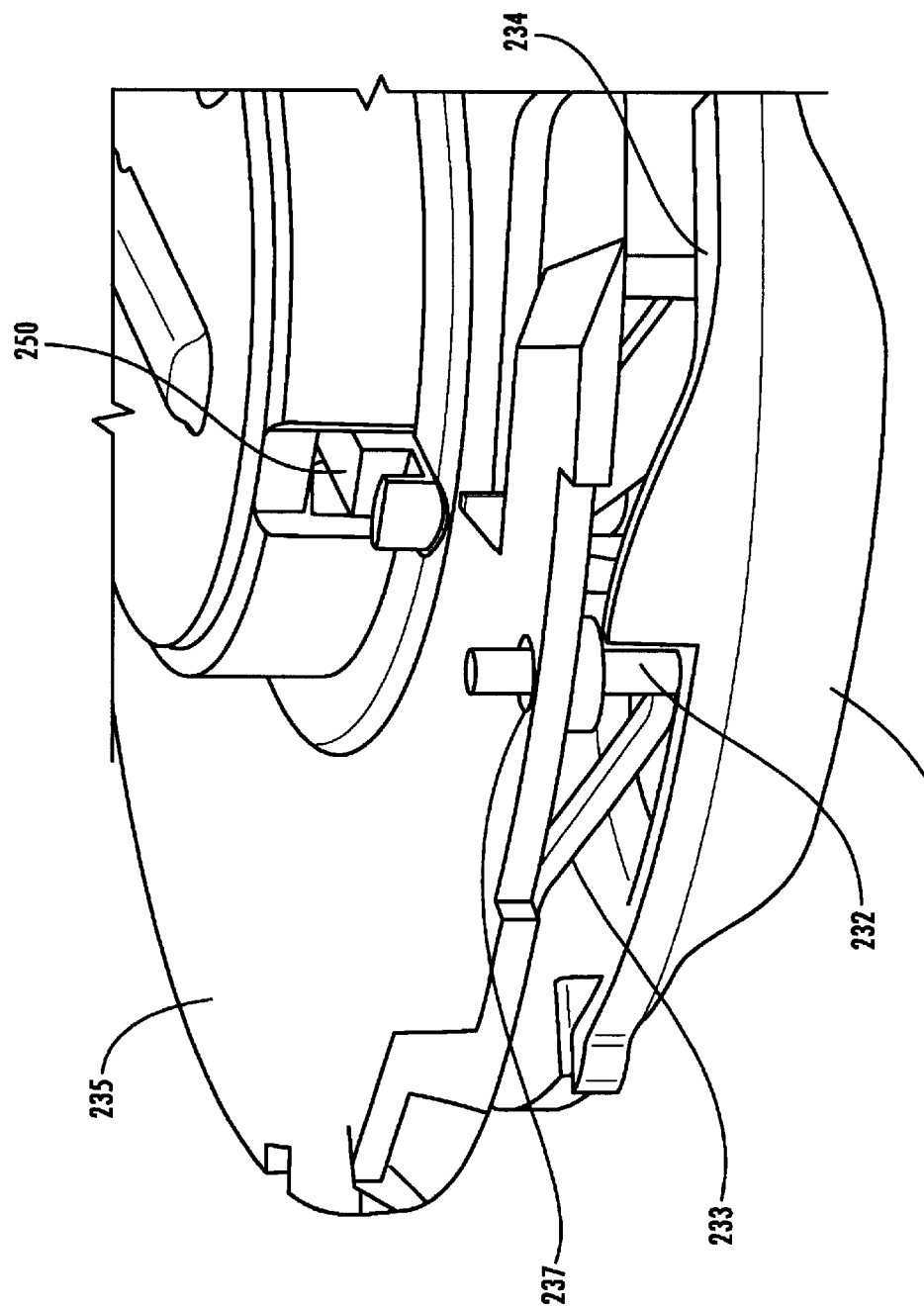
FIG. 6 is a partial perspective view of an advancer mechanism of the lancing device for use with the cartridge of FIG. 4, showing a spring-loaded cap-displacing plunger driven by a cam surface of the advancer mechanism.
Figure 9:
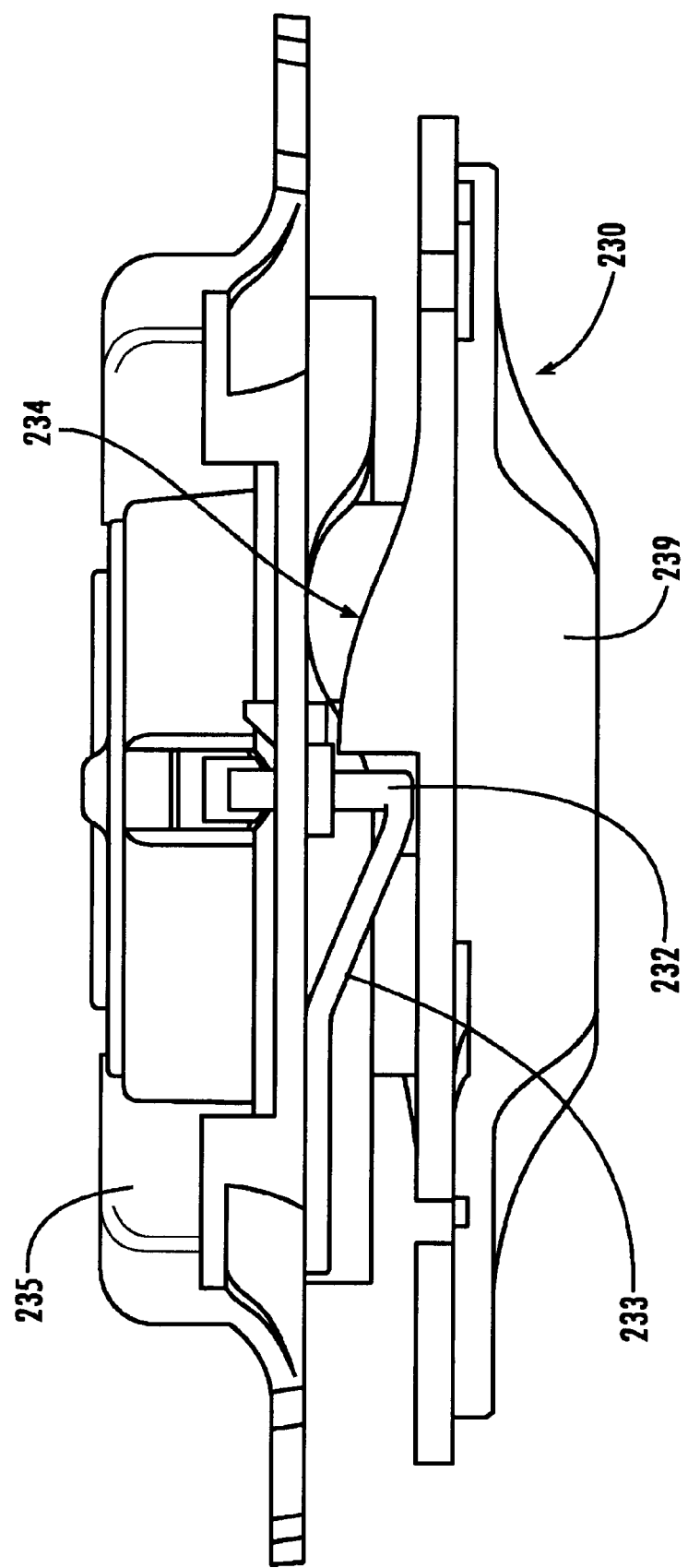
FIG. 9 is a side view of the advancer mechanism of FIG. 6, showing the spring-biased cam-driven plunger reset to a position clear of the lancing stroke travel path.

In this embodiment, however, the lancet cap displacement mechanism is provided by a spring-biased cam-driven plunger assembly. This assembly includes a plunger 232 that is positioned at about the cartridge outer perimeter and adjacent (beneath or above) the active lancet position. The plunger 232 is the form of a pin, shaft, tube, T-member, angle piece, or other elongated structure. With particular reference to FIGS. 6 and 9, the plunger 232 is ordinarily biased away from the active lancet (e.g., downwardly) under the influence of a spring element 233. The spring element 233 may be provided by a cantilevered leaf spring arm that is attached to (and integrally formed with) the plunger 232, as shown. Alternatively, the spring element may be provided by a coil spring (e.g., coaxially arranged with the plunger), an elastic member (e.g., rubber band), or other biasing structure. In the depicted embodiment, the plunger 232 extends through an opening 235 in the upper shell 237 of the advancing mechanism 230, and the spring element 233 is attached to the upper shell and the plunger.

The spring-biased cam-driven plunger assembly further comprises a cam surface 234 formed, for example, on the lower shell 239 of the advancer mechanism 230 of the lancing device. Preferably, the cam surface 234 is generally wedge-shaped, as shown, with two of the wedges arranged at about 180 degrees apart, though other specific shapes, numbers, and spacings of the cams may be used. As the advancer mechanism 230 is actuated, a follower surface of the plunger 232 traverses along the cam surface 234. The plunger 232 rises as it moves along the upwardly inclined portion of the cam surface 234, at the same time charging the spring arm 233. As the plunger 232 rises, it is pressed into engagement with the cap 128 of the active lancet 120. The rising plunger 232 pushes the cap 128 upwardly along the cap guide tracks 131 of the carrier disk 118 along the transverse guide path at about 90 degrees relative to the lancing stroke travel path, and out of the radial path of the active lancet's lancing stroke. The cap guide tracks 131 are preferably resilient members (e.g., barbs or fingers) that retain the cap 128 above the path of travel of the active lancet, as seen best with reference to FIG. 8. Continued actuation of the advancer mechanism 230 moves the inclined portion of the cam surface 234 past the plunger 232, as seen best with reference to FIG. 9, allowing the plunger to drop back down under the influence of the charged spring arm 233. The plunger 232 is now reset and out of the active lancet's path of travel as it is propelled along its lancing stroke.

It will be understood that the spring-biased, cam-driven plunger assembly may be provided as part of one or more other components of the lancing device. For example, in an alternative embodiment the spring and plunger are attached to and extend upwardly from the housing bottom with the spring biased upwardly to displace the lancet caps. And the cam surface is formed on a rotary element (e.g., rotationally moved by the advancing mechanism) within the lancing device housing. The cam surface may be configured to drive the plunger downwardly away from the active lancet cap except when the lancet is charged and ready for activation, at which position the plunger moves under the influence of the spring to displace the cap. For example, the cam surface may be defined by two (or another number of) upwardly recessed notches that permit the plunger to move upward to displace the caps. In other alternative embodiments, the cam surface is defined on a stationary element and the plunger is rotated relative to the cam surface for driving the plunger to displace the lancet caps.

2. The Lancing Device

Figure 16:
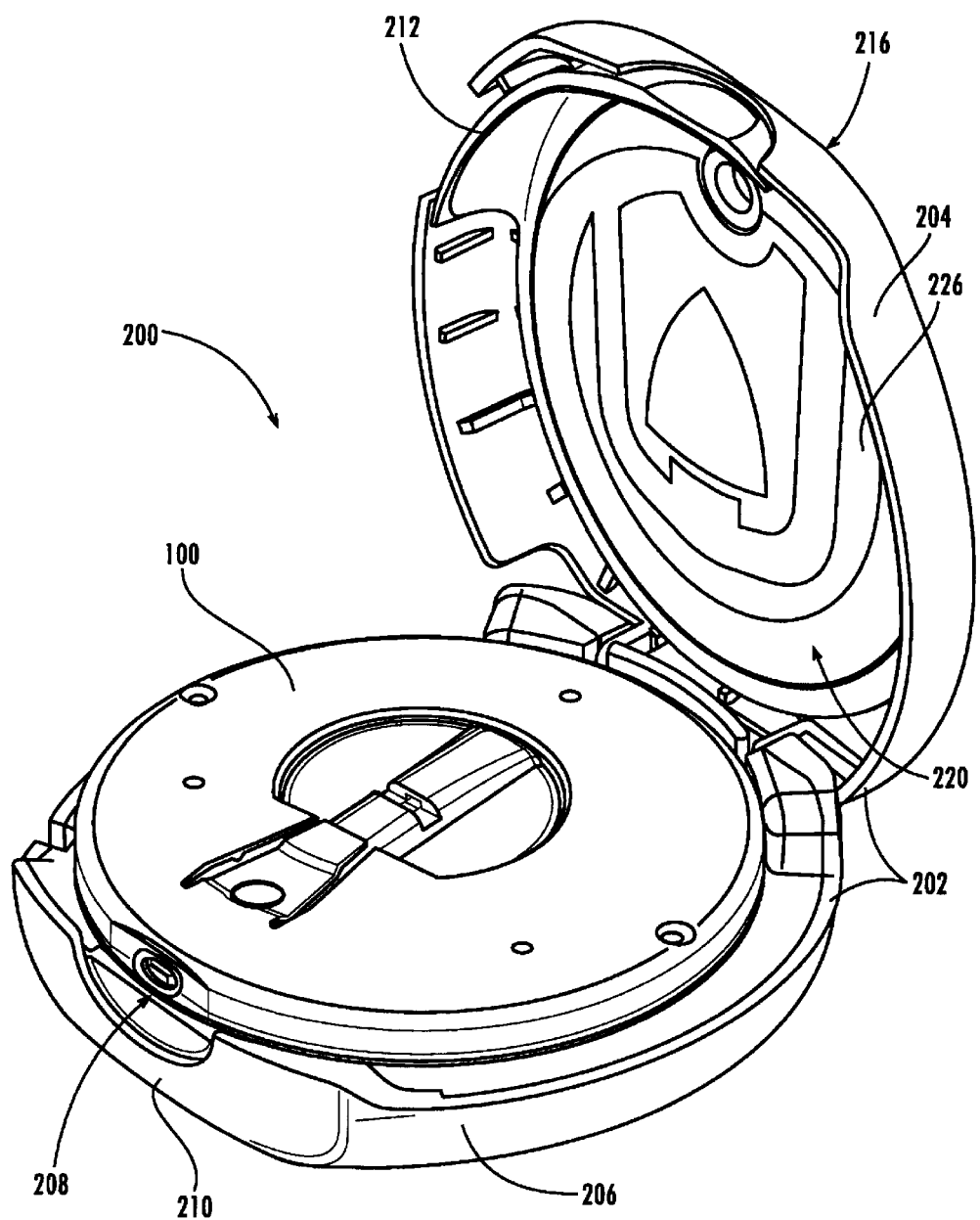
FIG. 16 is a perspective view of the cartridge of FIG. 4 installed in the lancing device of FIG. 7.

As shown in FIG. 16, a lancing device 200 according to an example embodiment of the present invention preferably comprises a clam-shell housing 202 having a top portion 204 hingedly connected to a bottom portion 206. The housing 202 defines a lancing opening 208, preferably through a sidewall portion 210 thereof, that aligns with the lancing opening 15 of an installed cartridge 100. The housing 202 preferably also comprises a latch 216 that secures the top 204 of the housing 202 to its bottom 206.

Figure 7:
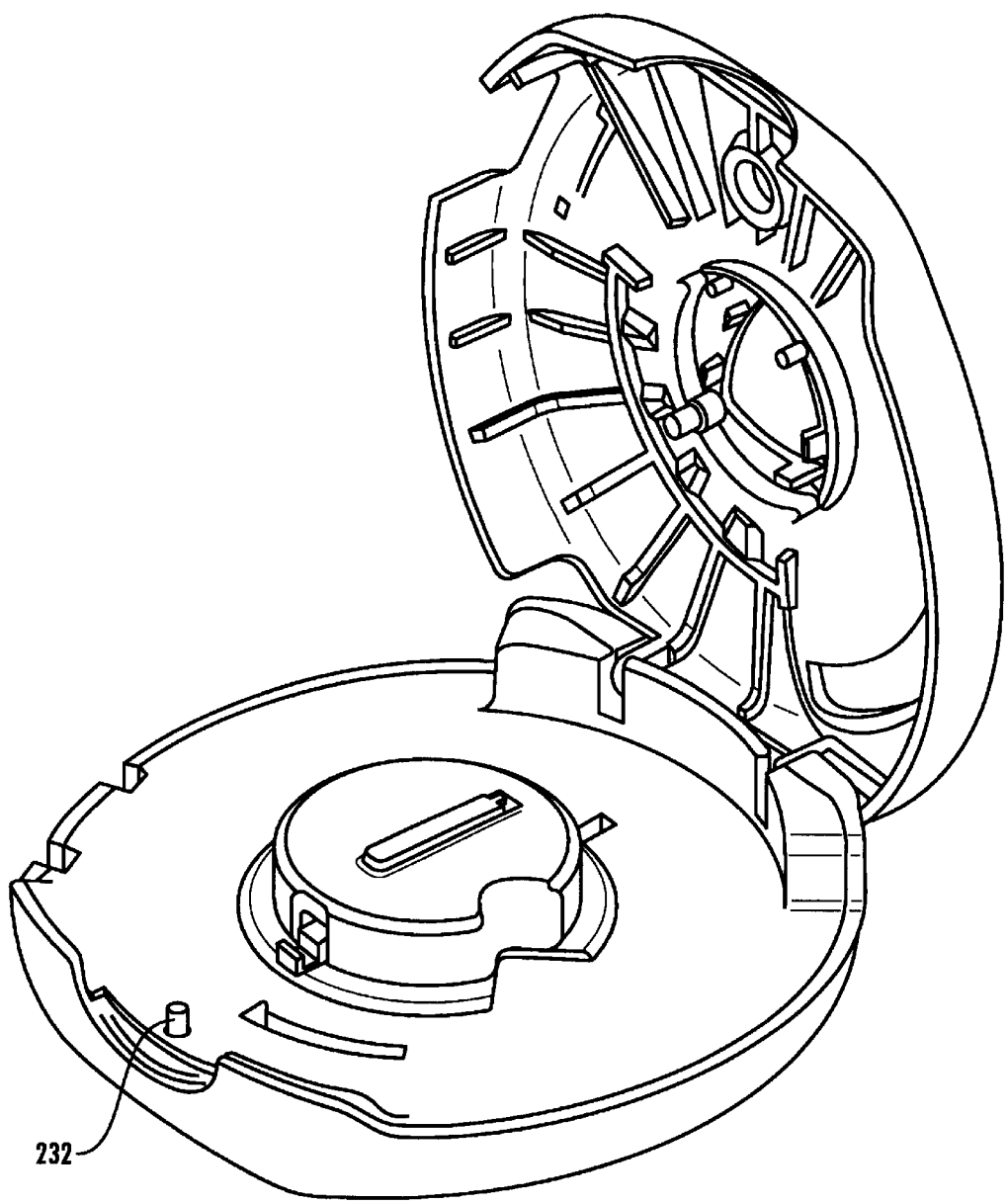
FIG. 7 is a perspective view of a lancing device according to the second example embodiment of the invention, suited for use with the cartridge assembly of FIG. 4, showing the lancing device in an opened position revealing the advancer mechanism of FIG. 6 situated therein, and showing the spring-loaded cam-driven plunger extending through the upper shell of the advancer mechanism.
Figure 8:
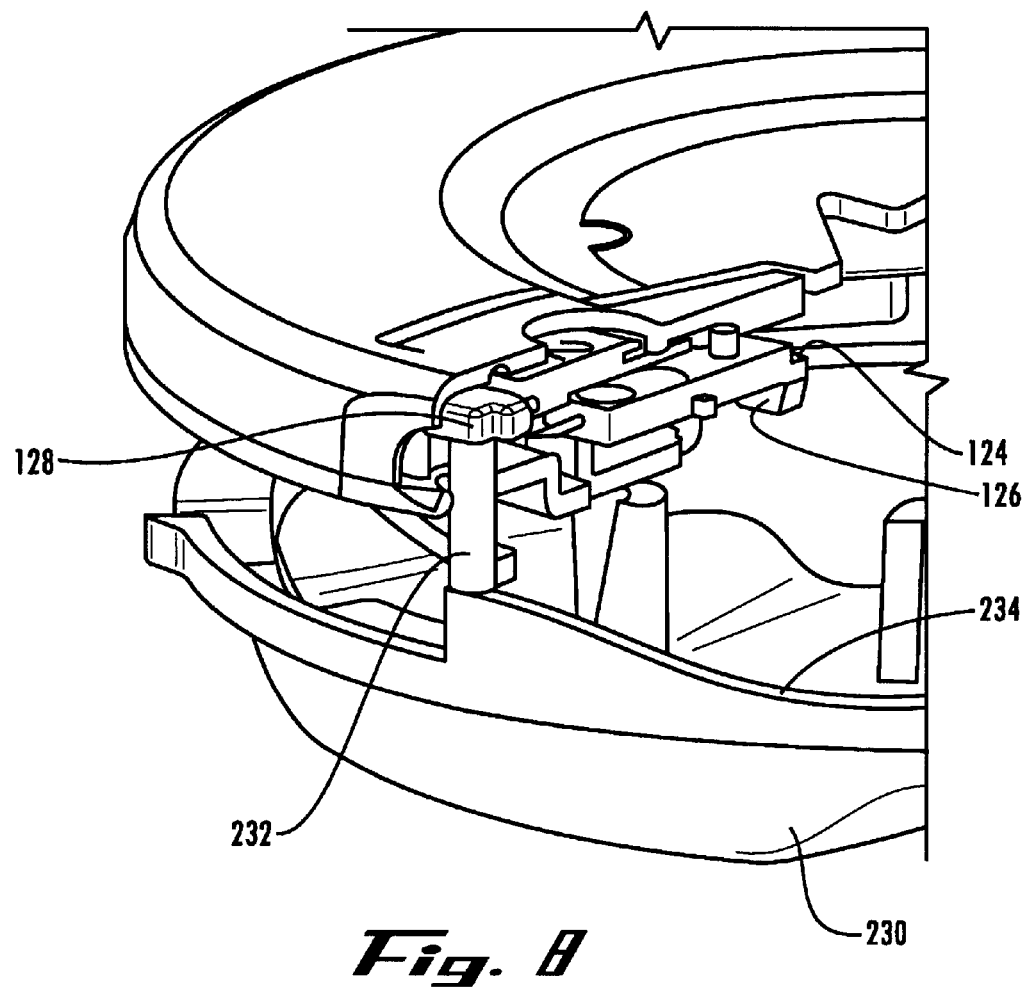
FIG. 8 is a partial cutaway perspective view of the advancer mechanism of FIG. 6, showing the spring-biased cam-driven plunger displacing a cap of an active-position lancet.
Figure 12:
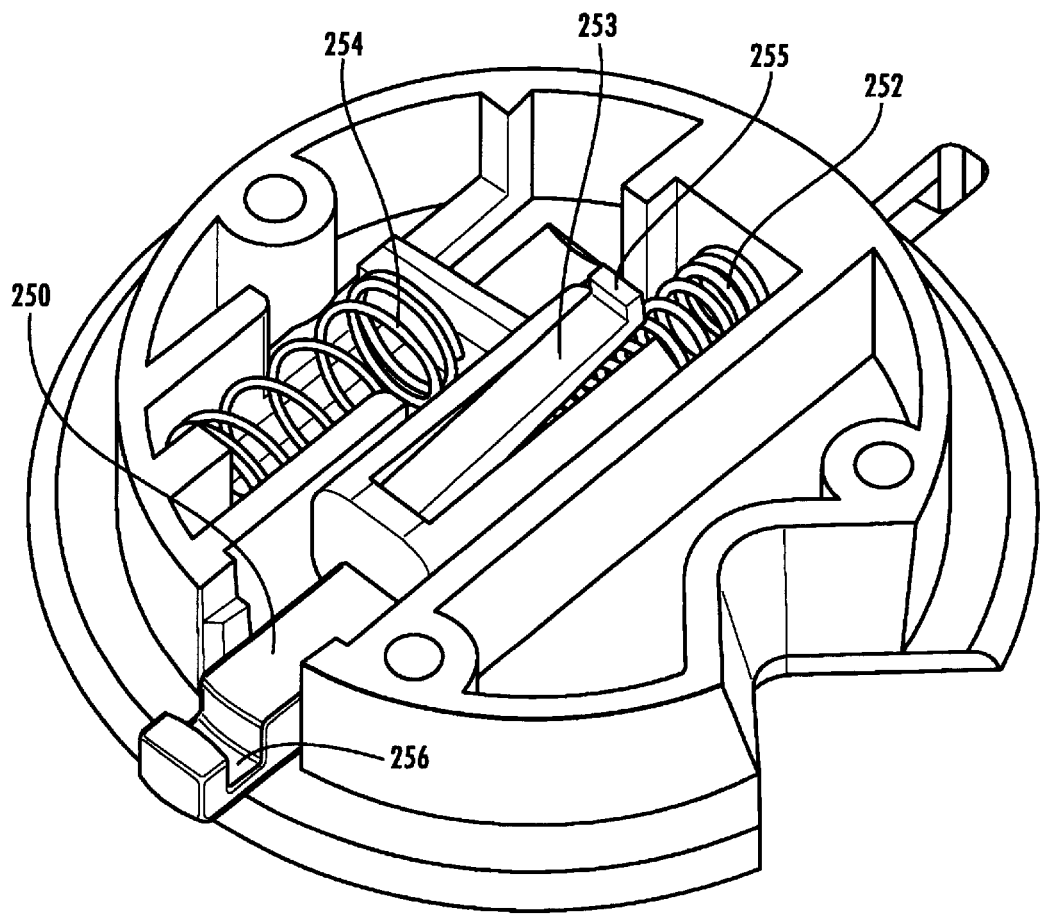
FIG. 12 is a perspective view of a drive and return mechanism of the lancing device of FIG. 7.

The lancing device preferably further comprises a drive mechanism, seen best with reference to FIGS. 7, 12, and 16. The drive mechanism preferably includes a reciprocating plunger 250 that engages the active lancet 20 and drives it radially along its lancing stroke upon activation or firing of the device, through an advanced position where the lancet tip punctures the subject's skin, and back to a retracted position where the lancet tip is shielded within the cartridge. The plunger 250 preferably comprises a recess forming a jaw 256 for receiving and engaging the foot 26 of the active lancet. In a preferred embodiment, two springs, a drive spring 252 and a return spring 254, operate in tandem to drive and return the plunger 250 upon activation of the lancing device by pressing the activating button 220. The springs can be, for example, coil springs, leaf springs, torsion springs, spiral springs, or the like, including other biasing mechanisms. The drive spring 252 is the stronger of the two springs, and drives the active lancet from its initial position into its extended position. The return spring 254 serves to retract the active lancet after lancing the skin. One or more limit members, such as posts or lugs optionally interact with one or both springs, and/or with other portion(s) of the drive mechanism, to more precisely define the equilibrium, retracted, and/or extended position(s) of the plunger. Because the jaw 256 of the plunger is open to the top, it securely but releasably engages the foot 26 of the active lancet to drive the lancet along its lancing stroke, yet allows the cartridge to be removed and replaced at any point during its use. The plunger 250 preferably further comprises a flexible release arm 253 having a catch portion 255 that retains the plunger in its armed state, with drive spring 252 energized prior to activation, and is released by the activating button upon actuation to propel the active lancet through its lancing stroke.

Figure 13:
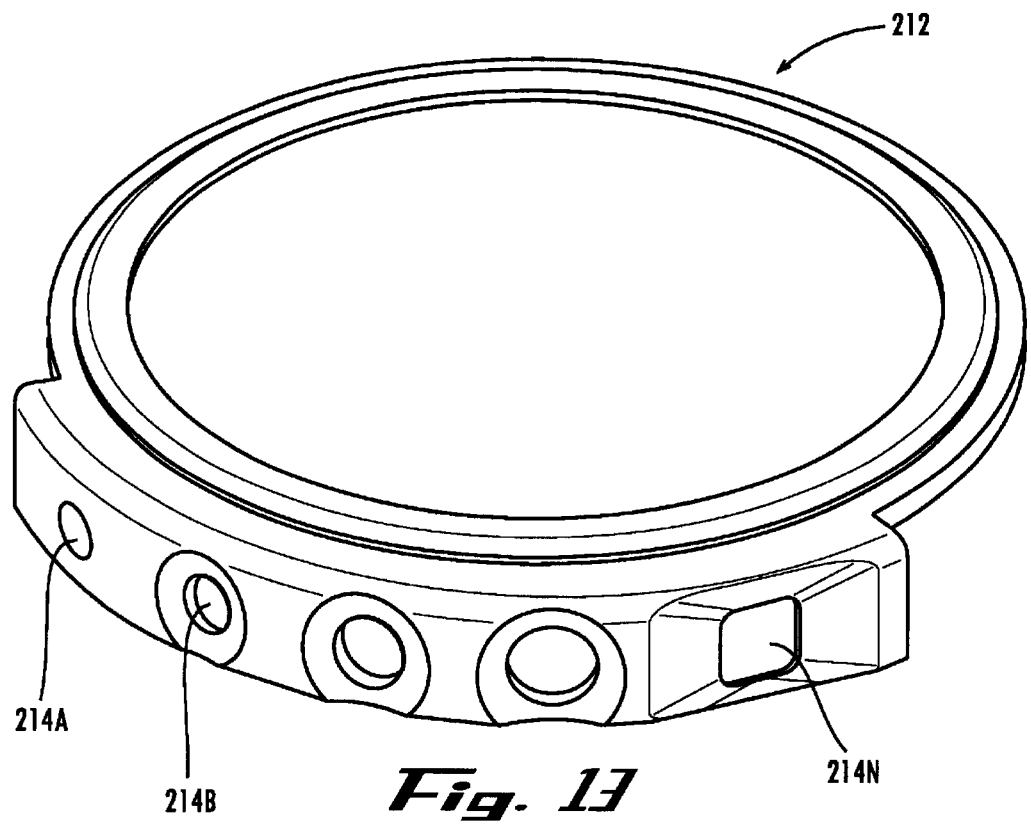
FIG. 13 is a perspective view of a lancing depth adjustment ring of the lancing device of FIG. 7.

The lancing device preferably further comprises a mechanism for depth control, in one embodiment a depth-control ring 212, shown in detail by FIG. 13. The depth ring 212 is positioned near the perimeter of the housing 202 of the lancing device 204, and generally follows the contour of the housing of the lancing device 200. The depth ring 212 defines a plurality of openings 214A, 214B . . . 214N (collectively, the "openings 214") therethrough, through which the tip of a lancet 20 is driven to pierce a skin surface of the subject to obtain a sample of blood. The openings 214 vary in diameter and/or in the depth to which their outer contact surfaces are recessed or countersunk. The depth ring 212 is rotated by the user to selectively position a particular opening 214 in alignment with the puncture position 208, thereby controlling the depth of penetration of the lancet tip into the subject's skin. Because the openings can vary in diameter and in recess depth, the depth ring 212 provides a wide range of depth control. The travel of the lancet 20 preferably is not affected by variation of the position of the depth ring 212, and so the lancing stroke preferably remains uniform regardless of the depth control position.

Figure 14:
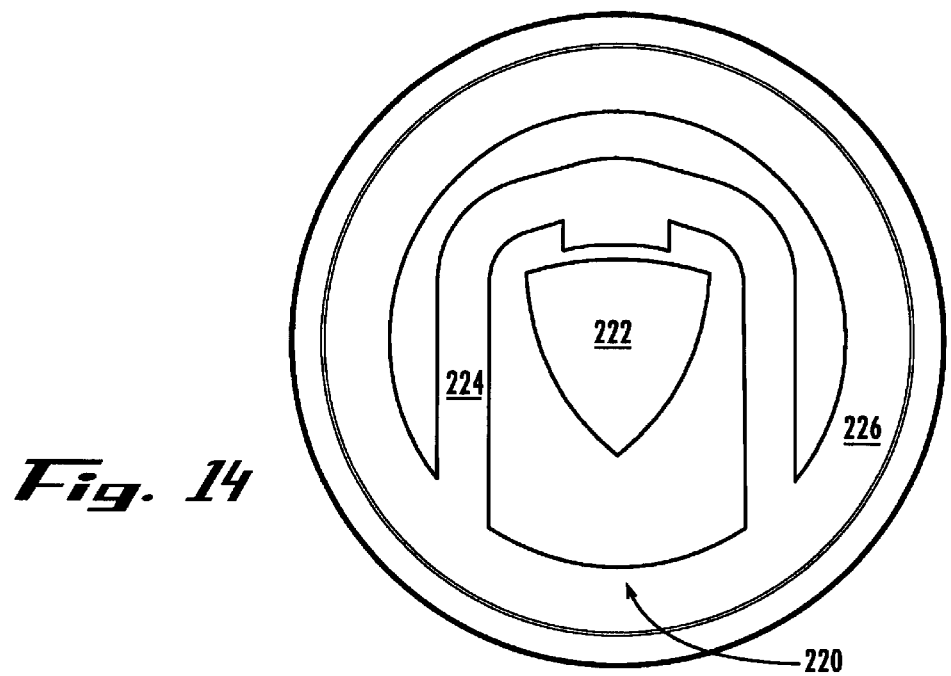
FIG. 14 is a top view of an actuator button portion of the lancing device of FIG. 7.
Figure 15A:
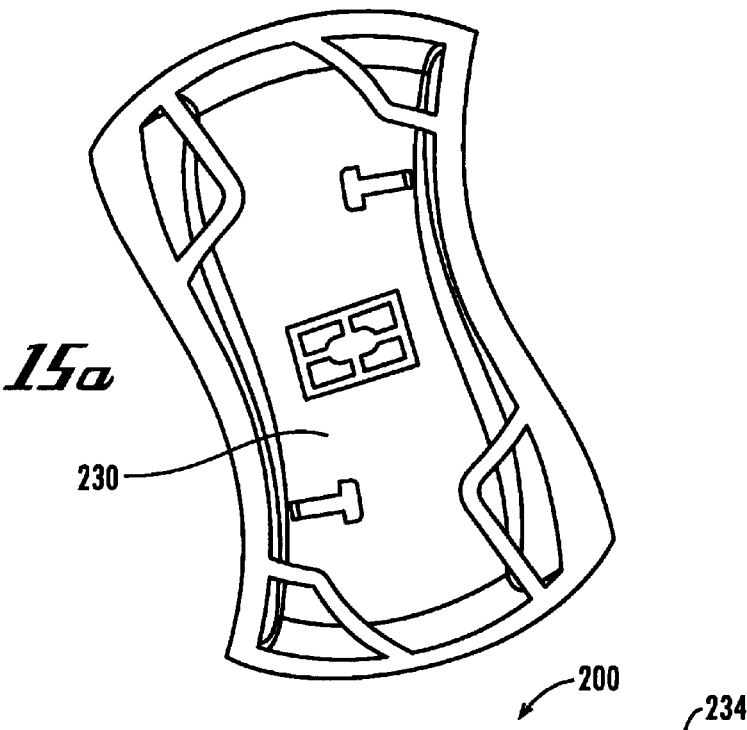
FIG. 15a is a detailed plan view of a portion of the advancer mechanism of FIG. 6 located on the bottom of the housing of the lancing device of FIG. 7.
Figure 15B:
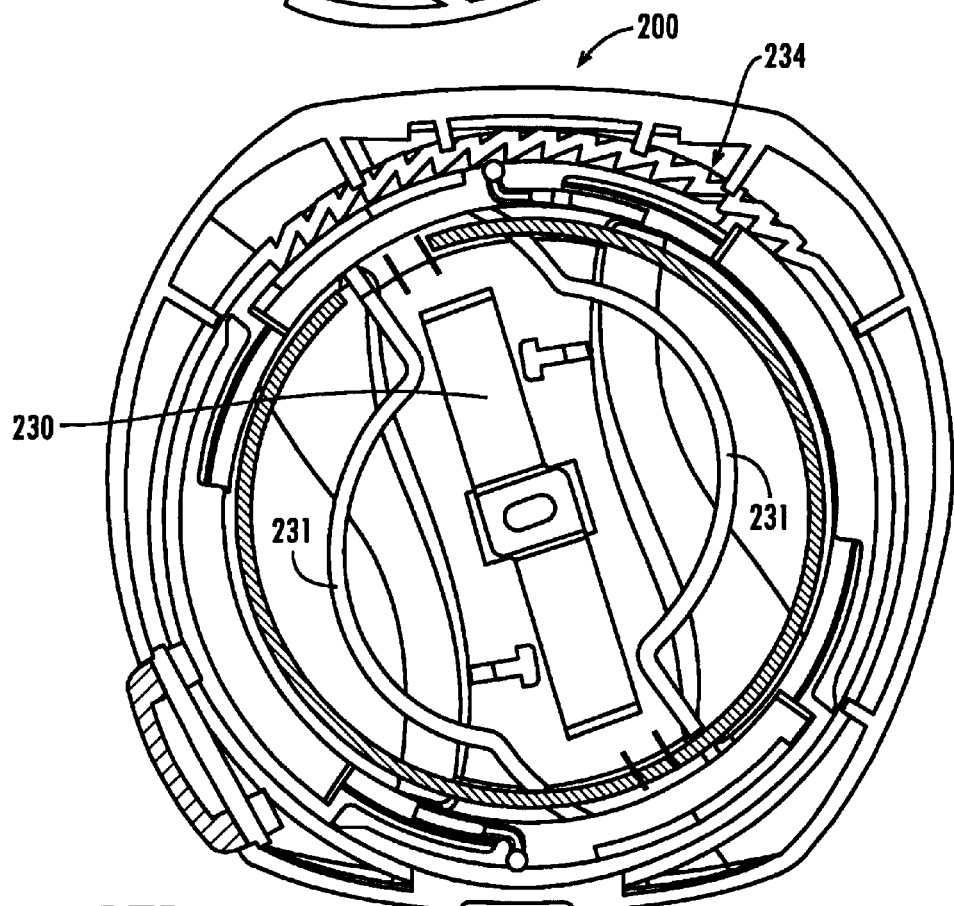

The lancing device preferably further comprises an activating button positioned on the top half-shell 204 of the housing 202 for activating the drive mechanism to propel the active lancet through its lancing stroke. An example configuration of the activating button member 220 is shown in FIG. 14. The activating button member 220 preferably includes a button portion 222, which releases the catch portion 255 of the plunger release arm when pressed by the user to activate or fire the device. The activating button member 220 preferably further comprises one or more integral spring arms 224 for biasing the button 222 outwardly. The activating button member 220 preferably further comprises a retainer ring for securing the depth control ring 212 in place.

The lancing device 200 preferably further comprises an advancer mechanism 230 as seen best with reference to FIGS. 8, 9, 15a, 15b, and 16. In preferred form, the advancer mechanism 230 generally comprises a manually-rotatable element that is operable to advance the carrier to move sequential lancets 20 of a lancet cartridge 118 into the active position. A finger preferably projects from the advancer mechanism 230 through a slot in the bottom housing of the lancet cartridge to engage and advance the lancet carrier through indexed rotational increments corresponding to one lancet position, while the outer housing of the lancet cartridge remains fixed in position. Actuation of the advancer mechanism 230 preferably also functions to engage the active lancet in the jaw of the plunger and retract the plunger to de-cap the active lancet and energize or arm the drive mechanism.

Figure 10:
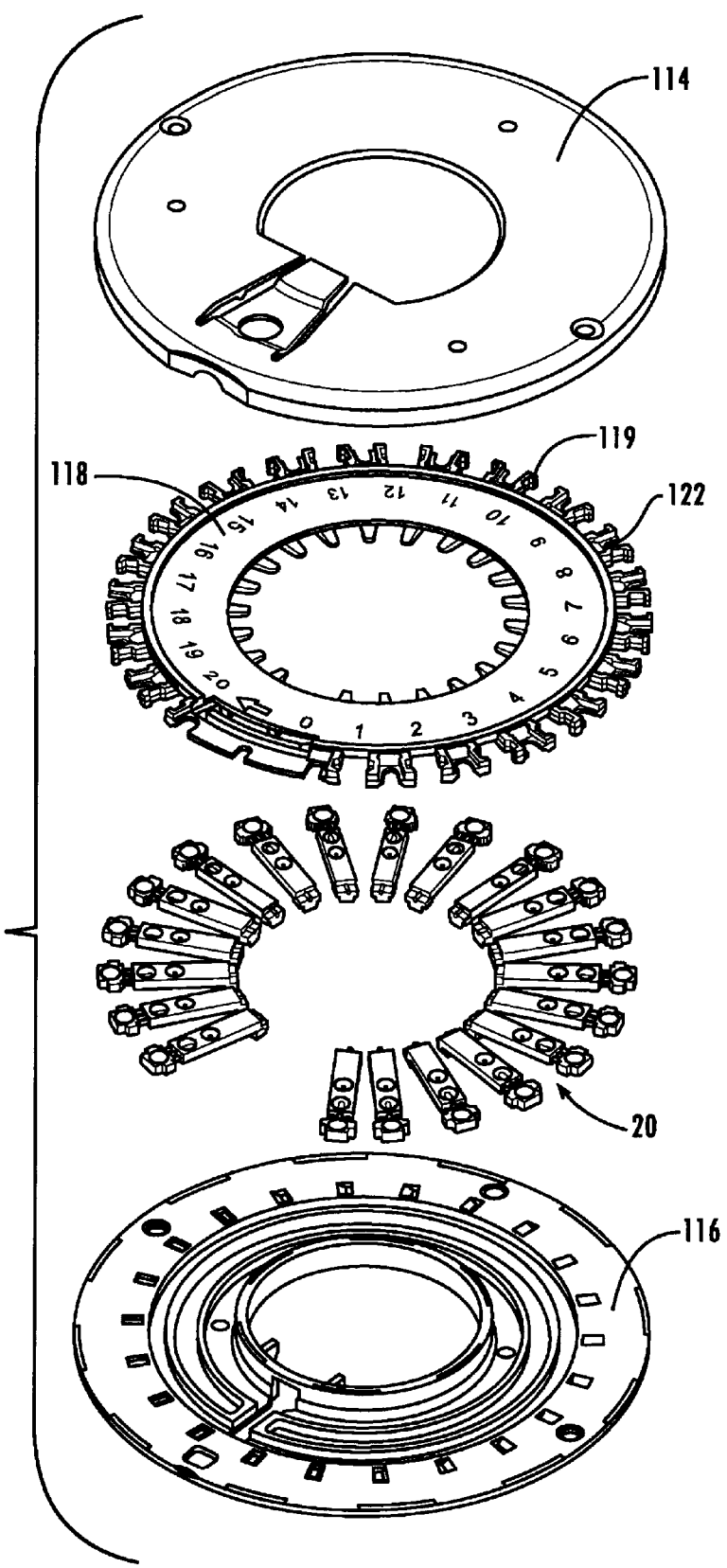
FIG. 10 is another exploded perspective view of the cartridge assembly of FIG. 4.
Figure 11:
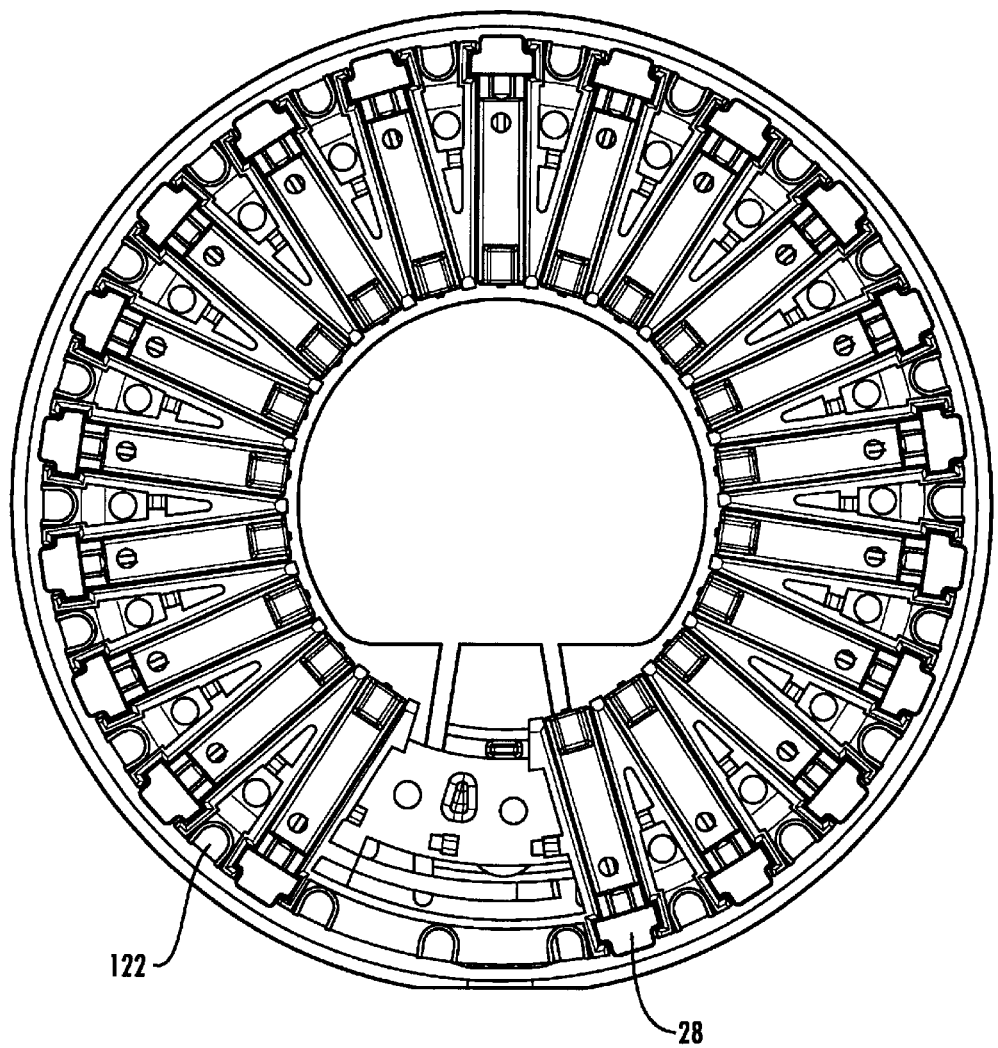
FIG. 11 is a bottom view of the cartridge assembly of FIG. 10 with the bottom cover removed for clarity.

Actuation of the advancer mechanism 230 may also serve to drive the spring-biased cam-driven plunger 232, as described above, if implementing the second example embodiment. Preferably, the advancer mechanism 230 is operable to rotate in one direction only and in discrete increments (e.g., 180° increments). Guide channels or ribs 231 formed in or on the inner face of the advancer mechanism act as cam paths to engage a cooperating follower element of the drive mechanism to retract the drive plunger 250 into its armed state, with drive spring 252 energized. Preferably, the guide channels or ribs 231 are contoured to retract the plunger 250 more slowly at the beginning of the advancing stroke, while the endcap 28 is being detached from the lancet, providing mechanical advantage for smoother and easier operation. A ratchet mechanism 234 may be provided to prevent reverse rotation of the advancer mechanism. Optionally, at the end of the advancing operation, a locating pin is driven upwardly (as by a cam surface similar to the motion of plunger 232 described above) through an opening in the cartridge housing and engaged within a yoke 122 (see FIGS. 10 and 11) between lancet paths on the carrier disk 118, to more precisely position the active lancet and prevent further movement of the carrier disk until the lancing device is fired.

In further preferred embodiments, the carrier 118 comprises a groove 124 that engages a pin on the bottom portion of the housing of the cartridge assembly when all the lancets have been used. This groove and pin combination prevents the cartridge 100 from being moved in either direction after all of the lancets have been used, and thereby prevent a reuse of a non-sterile lancet.

Method of Operation

In operation, the user preferably releases a latch 216 to open the lancing device 200. The user then places a preassembled multi-lancet cartridge 100 into the lancing device 200 and closes and latches the housing 202. The user turns the advancer mechanism 230 through a 180° stroke. During the 180° rotation, the carrier 118 is indexed by one lancet position, thus indexing an unused lancet 20 into the active position. The plunger 250 engages foot 26 of the lancet and pulls the lancet radially inwardly. This step energizes the drive spring of the drive mechanism. The catch 255 of the plunger engages a cooperating surface feature of the housing, and the lancet is now in the energized or armed position.

As the lancet 20 is retracted radially inward to charge the drive spring, the cap 28 is held and prevented from moving radially inward with the lancet by the guide track (e.g., detents, fingers, or barbs) 119. In this way, the lancet cap 28 is separated from the lancet body 24. Then the cap displacement mechanism then moves the disengaged cap out of the travel path of the active lancet. In the first example embodiment, the spring arm 50 engages and moves the detached cap 28 out of the lancing stroke path where the cap is held by the guide track, and then the spring element returns to its reset or rest position clear of the lancing stroke. In the second example embodiment, the spring-biased cam-driven plunger 232 engages and moves the detached cap 28 out of the path of travel of the active lancet, then clears the cam and is biased back to its rest or reset position. The guide track (e.g., detents, fingers, or barbs) 119 capture the cap 28 and hold it above the path the lancet 20 will travel in the lancing stroke.

The user may adjust the depth ring 212 to the desired setting to vary the penetration depth. If present, the position lock pin is raised into engagement with the yoke 122 of the cartridge 118 to prevent further movement of the cartridge until activated or fired to release the active lancet to traverse its lancing stroke.

The lancing device 200 is positioned against a finger or other part of the subject's body. The activation button 220 is pressed, releasing the catch 255 of the plunger and allowing the drive spring 252 to drive the plunger 250 and the active lancet engaged in the jaw thereof along a controlled radial path, through an extended position where the lancet tip punctures the subject's skin at the lancing site. The lancet is preferably guided throughout its lancing stroke along three sides by the guide channels of the carrier 118 and on the fourth side by the cartridge housing. Upon reaching the extended position of the lancing stroke, the return spring 254 is energized to bias the plunger 250 and retract the lancet inwardly to a retracted position within the lancet cartridge.

While the invention has been described with reference to preferred and example embodiments, it will be understood by those skilled in the art that a variety of modifications, additions and deletions are within the scope of the invention, as defined by the following claims.

What is claimed is:

1. A lancing device for use with a cartridge having an array of lancets, each lancet including a detachable cap, the lancing device comprising:
    an advancing mechanism adapted to sequentially advance the lancets into an active lancet position;
    a drive mechanism having a drive member adapted to engage and retract an active-positioned one of the lancets to detach the corresponding active-positioned cap, and to drive the active-positioned lancet along a lancing stroke; and
    a cap-displacement mechanism including a cam-driven plunger adapted to engage and move the active-positioned and detached lancet cap in a direction perpendicular to the lancing stroke path of the active-positioned lancet; and
    a spring element that biases the plunger relative to the cap of the active-positioned lancet, and a cam surface that drives the plunger against the bias of the spring element and moves the plunger relative to the cap of the active-positioned lancet, wherein the plunger has a follower surface that transcribes the cam surface to drive the plunger upon movement of the cam surface relative to the plunger.

2. The lancing device of claim 1, wherein the spring element biases the plunger away from the cap of the active-positioned lancet.

3. The lancing device of claim 1, wherein the spring element biases the plunger away from the cap of the active-positioned lancet, and wherein the cam surface drives the plunger against the bias of the spring element and into engagement with the cap of the active-positioned lancet to displace the active-positioned and detached lancet cap from the lancing stroke path of the active-positioned lancet.

4. The lancing device of claim 1, wherein the cap-displacement mechanism is operably coupled to the advancing mechanism so that the operation of the advancing mechanism also operates the cap-displacement mechanism.

5. The lancing device of claim 1, further comprising a housing containing the advancing mechanism, the drive mechanism, and the cap-displacement mechanism, wherein the multi-lancet cartridge is replaceably received in the housing, wherein the plunger is extendible out through an opening in the lancing device housing and in through an opening in the cartridge to engage the cap of the active-positioned lancet.

6. The lancing device of claim 1, a plurality of guide tracks defining an array of transverse guide paths along which the lancet caps are displaced transversely from the lancing stroke path, and wherein the guide tracks are adapted to retain the lancet caps after displacement from the lancing stroke path.

7. A lancing device for use with a cartridge having an array of lancets, each lancet including a detachable cap, the lancing device comprising:
    an advancing mechanism adapted to sequentially advance the lancets into an active lancet position;
    a drive mechanism having a drive member adapted to engage and retract an active-positioned one of the lancets to detach the corresponding active-positioned cap, and to drive the active-positioned lancet along a lancing stroke; and
    a cap-displacement mechanism including a plunger with a follower surface, the plunger being biased away from the cap of the active-positioned lancet, and a cam surface, wherein the follower surface transcribes the cam surface upon movement of the cam surface relative to the plunger to drive the plunger into engagement with the cap of the active-positioned lancet to displace the active-positioned and detached lancet cap from the lancing stroke path of the active-positioned lancet.

8. The lancing device of claim 7, further comprising a spring element comprising a cantilevered leaf spring, wherein the spring element biases the plunger away from the cap.

9. The lancing device of claim 8, wherein the cantilevered leaf spring extends from the plunger.

10. The lancing device of claim 7, wherein the follower surface transcribes the cam surface upon rotary movement of the cam surface relative to the plunger.

11. The lancing device of claim 7, wherein the cam surface includes a plurality of ramped segments that drive the plunger as the plunger follower surface transcribes the ramped segments.

12. The lancing device of claim 7, wherein the cap-displacement mechanism is operably coupled to the advancing mechanism so that the operation of the advancing mechanism also operates the cap-displacement mechanism.

13. The lancing device of claim 7, a plurality of guide tracks defining an array of transverse guide paths along which the lancet caps are displaced transversely from the lancing stroke path, and wherein the guide tracks are adapted to retain the lancet caps after displacement from the lancing stroke path.

14. The cartridge assembly of claim 13, wherein the lancet caps define one or more cap guide surfaces that engage and ride along the guide tracks as the caps are displaced from the lancing stroke path.

15. The cartridge assembly of claim 14, wherein the guide tracks engage the cap guide surfaces to retain the active-positioned cap from being retracted with the active-positioned lancet so that the retained active-positioned cap separates from the retracted active-positioned lancet.

16. A lancing device for use with a cartridge having an array of lancets, each lancet including a detachable cap, the lancing device comprising:
    an advancing mechanism adapted to sequentially advance the lancets into an active lancet position;
    a drive mechanism having a drive member adapted to engage and retract an active-positioned one of the lancets to detach the corresponding active-positioned cap, and to drive the active-positioned lancet along a lancing stroke; and a cap-displacement mechanism including a cam-driven plunger, the cap-displacement mechanism being operably coupled to the advancing mechanism so that operation of the advancing mechanism also operates the cap-displacement mechanism to move the cam driven plunger into engagement with the active-positioned and detached lancet cap and move the active-positioned and detached lancet cap from the lancing stroke path of the active-positioned lancet.

* * * * *